(12) United States Patent
Vaiarello et al.

(10) Patent No.: US 11,318,312 B2
(45) Date of Patent: May 3, 2022

(54) HEARING DEVICE USING A COCHLEAR IMPLANT SYSTEM AND CONTROL METHOD THEREOF

(71) Applicant: Oticon Medical A/S, Smørum (DK)

(72) Inventors: Yannick Vaiarello, Vallauris (FR); Pierre Stahl, Vallauris (FR); Michel Hoen, Vallauris (FR); Dan Gnansia, Vallauris (FR)

(73) Assignee: Oticon Medical A/S, Smørum (DK)

( * ) Notice: Subject to any disclaimer, the term of this patent is extended or adjusted under 35 U.S.C. 154(b) by 301 days.

(21) Appl. No.: 16/523,716

(22) Filed: Jul. 26, 2019

(65) Prior Publication Data

US 2020/0030611 A1 Jan. 30, 2020

(30) Foreign Application Priority Data

Jul. 27, 2018 (EP) ...................................... 8186067

(51) Int. Cl.
*A61N 1/36* (2006.01)
*A61N 1/05* (2006.01)
(Continued)

(52) U.S. Cl.
CPC ....... *A61N 1/36142* (2013.01); *A61N 1/0541* (2013.01); *A61N 1/14* (2013.01);
(Continued)

(58) Field of Classification Search
CPC ............ A61N 1/36142; A61N 1/36038; A61N 1/0541; A61N 1/14; A61N 1/36157; A61N 1/36185; H04R 25/505; H04R 2225/67
See application file for complete search history.

(56) References Cited

U.S. PATENT DOCUMENTS

| 5,522,865 A * | 6/1996 | Schulman | .......... | A61N 1/36038 |
|---|---|---|---|---|
| | | | | 607/56 |
| 2004/0082980 A1* | 4/2004 | Mouine | .............. | A61N 1/36039 |
| | | | | 607/48 |

(Continued)

FOREIGN PATENT DOCUMENTS

EP 0 247 649 A1 12/1987

OTHER PUBLICATIONS

Extended European Search Report issued in European Patent Application No. 18186067.7, dated Jan. 15, 2019.

*Primary Examiner* — Lindsey G Wehrheim
(74) *Attorney, Agent, or Firm* — Birch, Stewart, Kolasch & Birch, LLP

(57) ABSTRACT

A hearing device for use with a cochlear implant system is disclosed. An input portion receives, as a stimulus, an acoustic signal, converts the acoustic signal into an electrical acoustic signal and provides the electrical acoustic signal. A processing portion processes the electrical acoustic signal and conducts an active grounding procedure. An implant portion being implantable at least partially in a cochlea of the user comprises a plurality of operation electrodes and a reference electrode, e.g. an external electrode being grounded and implantable outside of the cochlea of the user. The operation electrodes are driven by the processing portion on the basis of the electric acoustic signal. An electrode state setting section sets the plurality of operation electrodes into one of a high impedance state, a grounded state and a stimulating state in which a signal based on the electric acoustic signal is supplied to a stimulation electrode of the plurality of operation electrodes. An electrode state setting pattern determining section selects, according to an operation mode of the cochlear implant system, one of a plurality of electrode state setting patterns, wherein each of the electrode state setting patterns is adapted to enable a stimu- (Continued)

lation by a stimulation electrode of the plurality of operation electrodes being in a stimulating state and at least one of the plurality of operation electrodes being in a grounded state or in a high impedance state. The electrode state setting section sets the plurality of operation electrodes into the specified electrode state according to the selected electrode state setting pattern.

17 Claims, 9 Drawing Sheets

(51) Int. Cl.
  *A61N 1/14* (2006.01)
  *H04R 25/00* (2006.01)
(52) U.S. Cl.
  CPC ..... *A61N 1/36038* (2017.08); *A61N 1/36157* (2013.01); *A61N 1/36185* (2013.01); *H04R 25/505* (2013.01); *H04R 2225/67* (2013.01)

(56) References Cited

U.S. PATENT DOCUMENTS

| | | |
|---|---|---|
| 2012/0191161 A1 | 7/2012 | van Dijk |
| 2018/0140838 A1 | 5/2018 | Smith |

\* cited by examiner

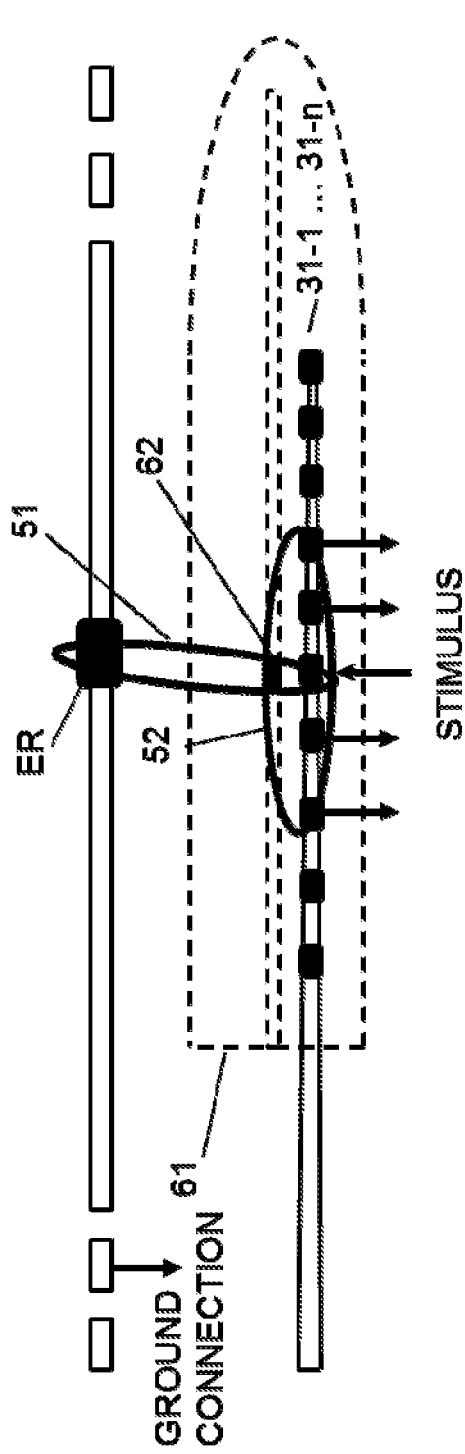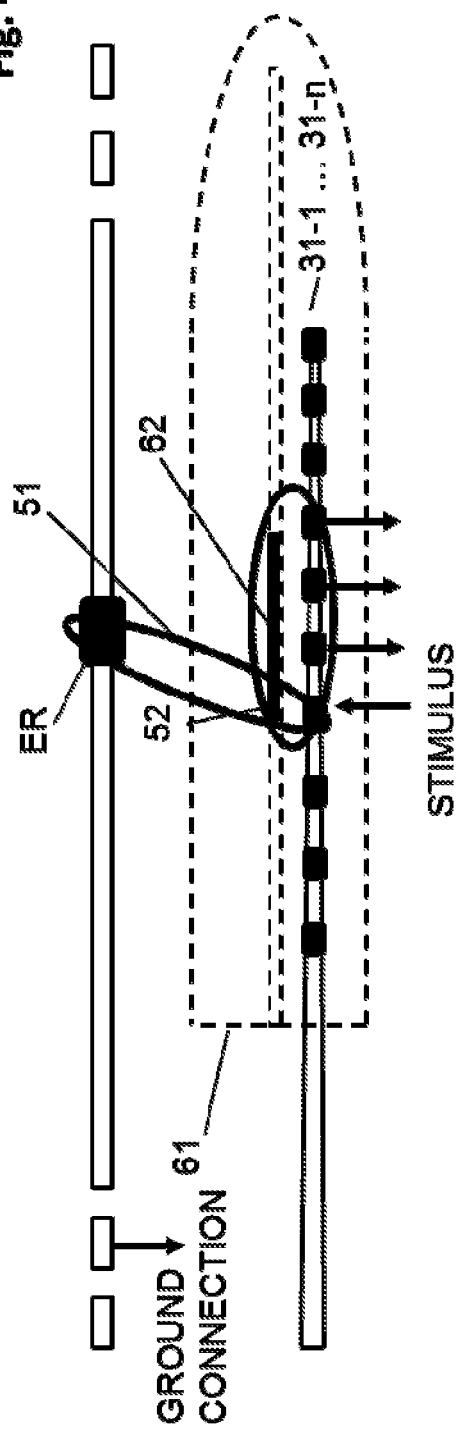

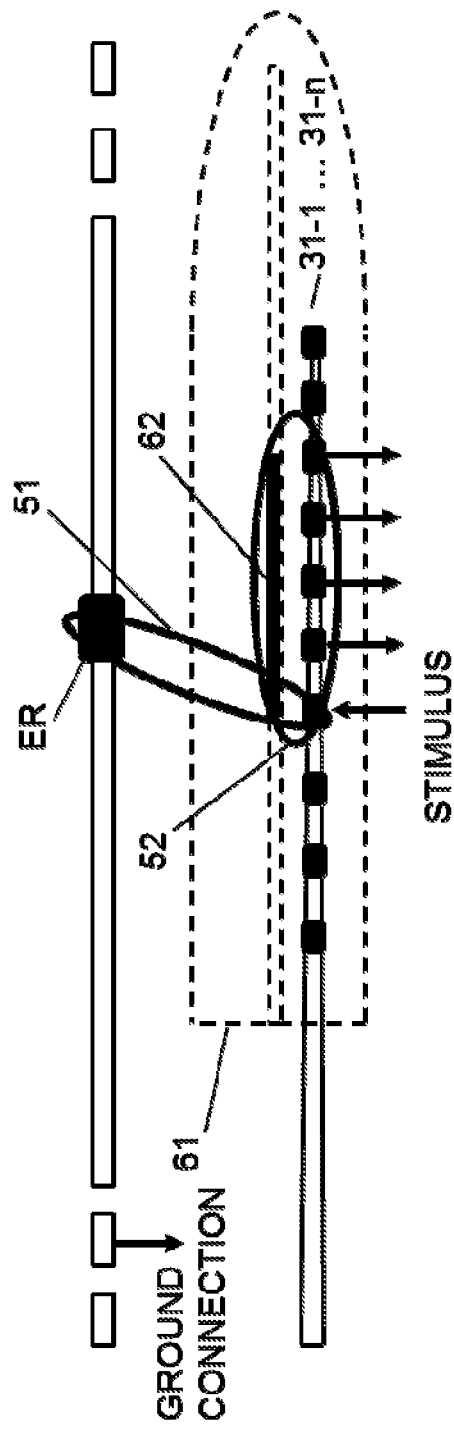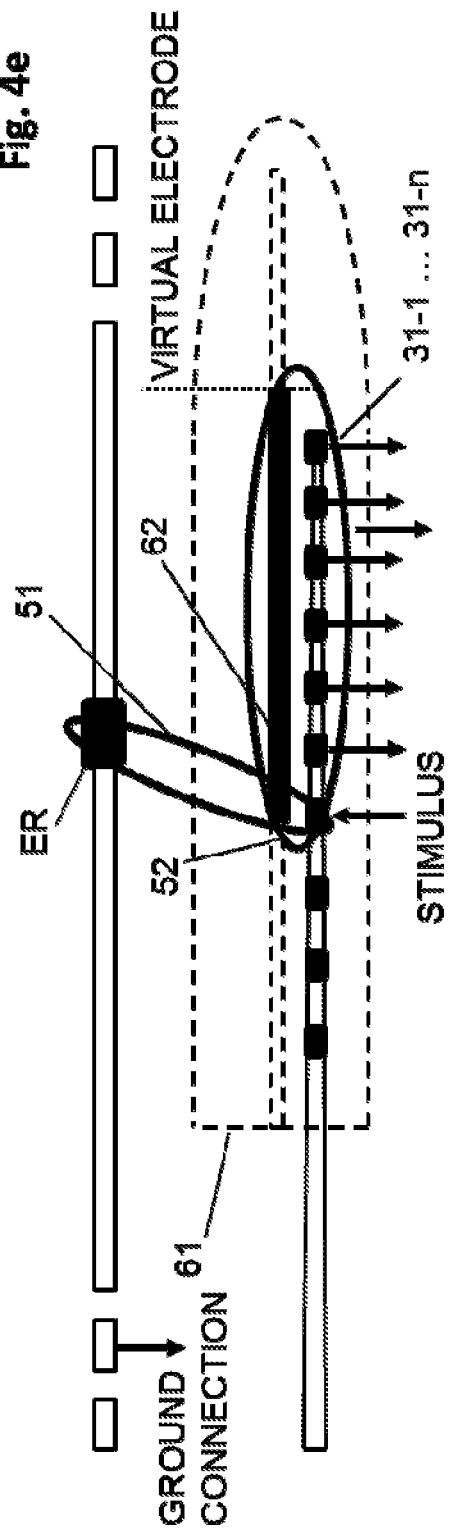

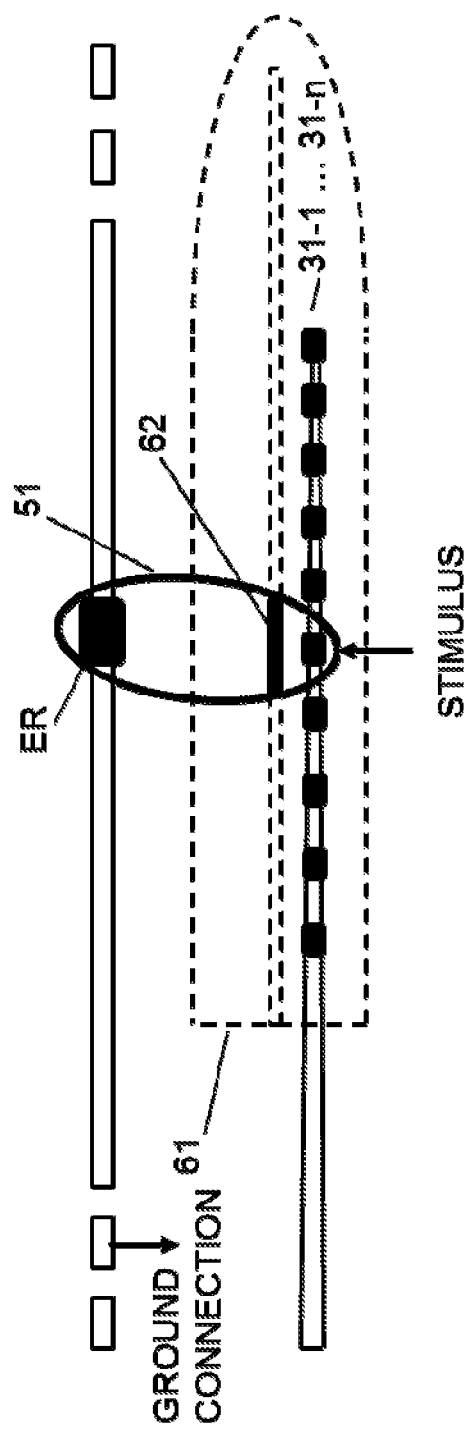

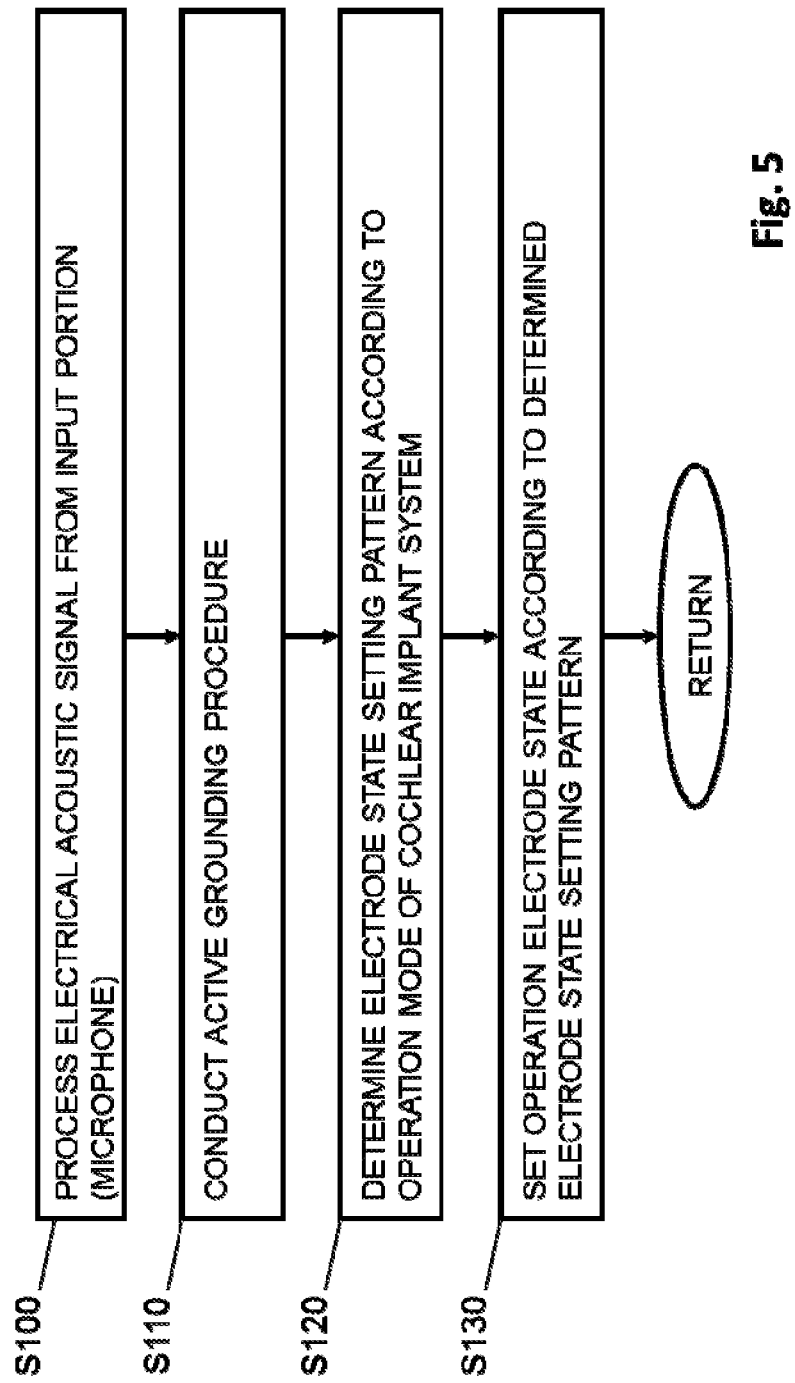

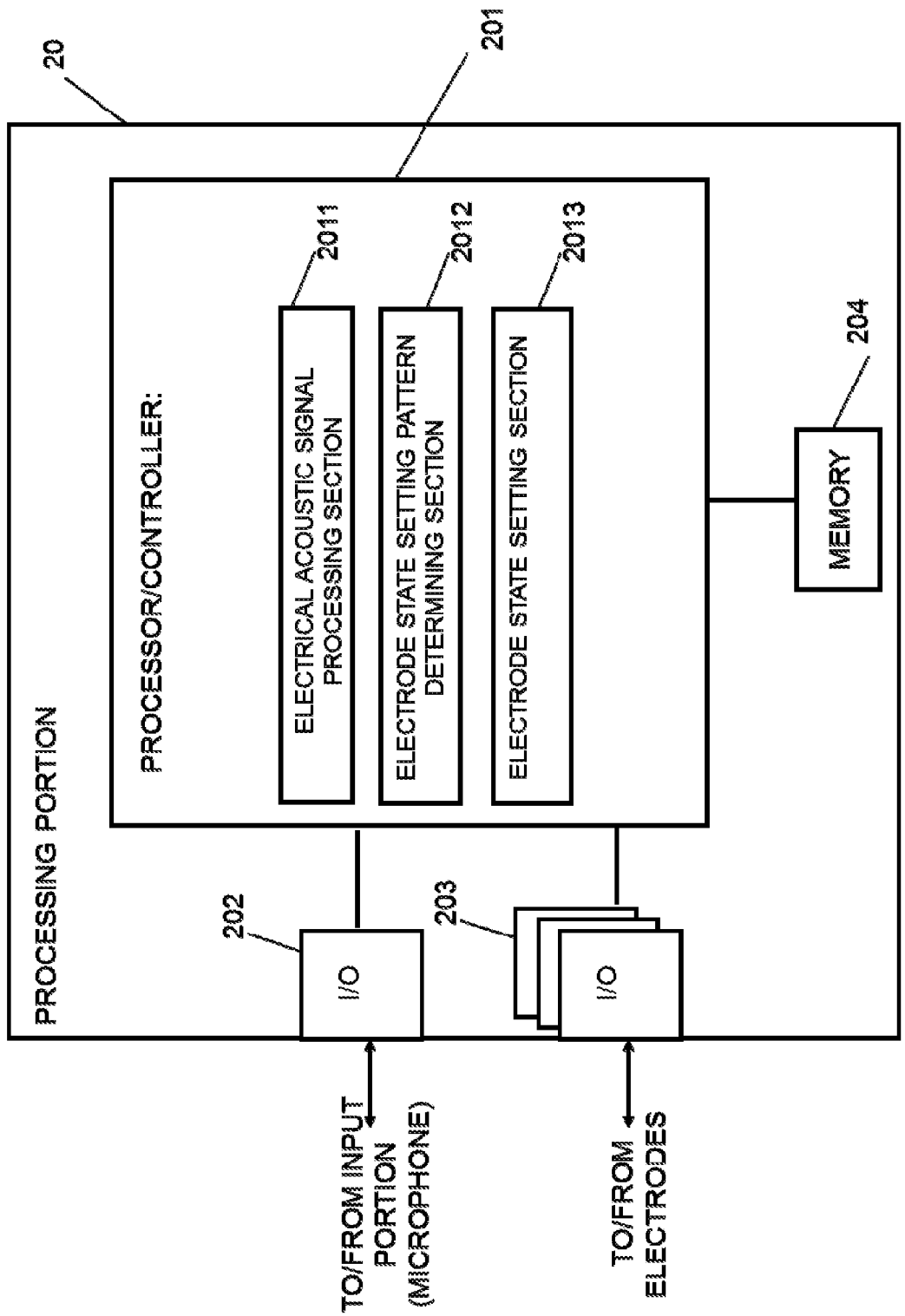

HEARING DEVICE USING A COCHLEAR IMPLANT SYSTEM AND CONTROL METHOD THEREOF

FIELD

The present disclosure relates to a hearing device using a cochlear implant system and a control method thereof. More particularly, the disclosure relates to measures for controlling electrode states of a cochlear implant system.

BACKGROUND

One issue in cochlear implant systems is that electrical field generated during activation of any electrode may widely spread into the cochlea. This can result in broad and unfocused excitations of auditory nerve fibers, which can deteriorate sound or speech recognition performance of a user of the hearing device.

The present disclosure provides at least an alternative to the prior art for controlling a hearing device using a cochlear implant system.

SUMMARY

According to an aspect, there is disclosed a hearing device for use with a cochlear implant system configured to improve or augment a hearing capability of a user. The hearing device comprises an input portion configured to receive, as a stimulus, an acoustic signal, to convert the acoustic signal into an electrical acoustic signal and to provide the electrical acoustic signal for further processing. A processing portion processes the electrical acoustic signal and conducts an active grounding procedure defined further below. In an implant portion which is implantable at least partially in a cochlea of the user, a plurality of operation electrodes for electrically stimulating different frequency ranges and a reference electrode part including at least one external electrode being grounded and implantable outside of the cochlea of the user are included. The plurality of operation electrodes are driven by the processing portion on the basis of the electric acoustic signal. For this, the processing portion comprises an electrode state setting section configured to set the plurality of operation electrodes into one of a high impedance state, a grounded state and a stimulating state in which a signal based on the electric acoustic signal is supplied to a stimulation electrode of the plurality of operation electrodes. Furthermore, the processing portion comprises an electrode state setting pattern determining section configured to select, according to an operation mode of the cochlear implant system, one of a plurality of electrode state setting patterns, wherein each of the electrode state setting patterns is adapted to enable a stimulation by a stimulation electrode of the plurality of operation electrodes being in a stimulating state and at least one of the plurality of operation electrodes being in a grounded state or in a high impedance state. The electrode state setting section causes setting of the plurality of operation electrodes into a specified electrode state of the high impedance state, the grounded state and the stimulating state according to the selected electrode state setting pattern.

According to another aspect, there is provided a control method for a hearing device for use in a cochlear implant system configured to improve or augment a hearing capability of a user. The hearing device comprises an input portion configured to receive, as a stimulus, an acoustic signal, to convert the acoustic signal into an electrical acoustic signal and to provide the electrical acoustic signal, a processing portion which processes the electrical acoustic signal and conducts an active grounding procedure, an implant portion configured to be implantable at least partially in a cochlea of the user and comprising a plurality of operation electrodes for electrically stimulating different frequency ranges, and a reference electrode part including at least one external electrode being grounded and implantable outside of the cochlea of the user. The plurality of operation electrodes are driven by the processing portion on the basis of the electric acoustic signal. According to the control method, an electrode state setting pattern is determined for selecting, according to an operation mode of the cochlear implant system, one of a plurality of electrode state setting patterns, wherein each of the electrode state setting patterns is adapted to enable a stimulation by a stimulation electrode of the plurality of operation electrodes being in a stimulating state and at least one of the plurality of operation electrodes being in a grounded state or in a high impedance state. Furthermore, the plurality of operation electrodes are set, according to the selected electrode state setting pattern, into a specified electrode state of a high impedance state, a grounded state and a stimulating state in which a signal based on the electric acoustic signal is supplied to a stimulation electrode of the plurality of operation electrodes.

According to further refinements, these examples may include one or more of the following features:

An operation mode determining portion may determine in which operation mode the cochlear implant system currently is or estimate in which operation mode the cochlear implant system is going to be in a predetermined time period; a processing for the determination of the operation mode may consider at least one parameter of a property of an input electrical acoustic signal, an implantation state of the plurality of operation electrodes, a functional state of each of the plurality of operation electrodes, an instruction input into a configuration setting, and an entering into a low power operation mode. This allows to consider different conditions which presently exist or will probably exist in the near future for improving the performance of the hearing device.

The operation mode of the cochlear implant system may comprise at least one of: a safety mode related to a situation where the plurality of operation electrodes are partially inserted into the cochlea and set into a high impedance state, a focused mode related to a situation where a current flow is to be focused on a specific part of the cochlea using a symmetrical setting of operation electrodes into the grounded state, a steering mode related to a situation where a current flow is to be directed to a specific part of the cochlea by steering an electrical field using an asymmetrical setting of operation electrodes into the grounded state, a virtual electrode mode related to a situation where a current flow is to be directed to a part of the cochlea not overlapping the implant portion using an asymmetrical setting of operation electrodes into the grounded state, and a passive full-monopolar mode related to a situation where a current flow is to be passively discharged. This allows to adapt the control scheme selected for the hearing device to various operation conditions and allows to enhance the performance of the hearing device.

The electrode state setting pattern determining section may select as an electrode state setting pattern at least one of: in case the operation mode of the cochlear implant system is the safety mode, an electrode state setting pattern causing to set at least one of the plurality of operation electrodes into the stimulated state according to the electrical acoustic signal, and to set all electrodes of the plurality of operation electrodes being located outside the cochlea into the high impedance state, in case the operation mode of the cochlear implant system is the focused mode, an electrode state setting pattern causing to set at least one of the plurality of operation electrodes into the stimulated state according to the electrical acoustic signal, to symmetrically set at least two of the plurality of operation electrodes being adjacent to the stimulated electrode into the grounded state, and to set the remaining electrodes of the plurality of operation electrodes into the high impedance state, in case the operation mode of the cochlear implant system is the steering mode, an electrode state setting pattern causing to set at least one of the plurality of operation electrodes into the stimulated state according to the electrical acoustic signal, to asymmetrically set at least two of the plurality of operation electrodes being located on one side of the stimulated electrode into the grounded state, and to set the remaining electrodes of the plurality of operation electrodes into the high impedance state, in case the operation mode of the cochlear implant system is the virtual electrode mode, an electrode state setting pattern causing to set at least one of the plurality of operation electrodes into the stimulated state according to the electrical acoustic signal, to set each electrode of the plurality of operation electrodes being located on one side of the stimulated electrode towards the distal end of the implant portion into the grounded state, and to set the electrodes of the plurality of operation electrodes being located on the other side of the stimulated electrode into the high impedance state, in case the operation mode of the cochlear implant system is the passive full-monopolar mode, an electrode state setting pattern causing to set at least one of the plurality of operation electrodes into the stimulated state according to the electrical acoustic signal, and to set the remaining electrodes of the plurality of operation electrodes into the high impedance state.

The electrode state setting section may set the plurality of operation electrodes into the grounded state by causing connecting the respective operation electrode to a common ground of the hearing device, into the stimulating state by connecting the respective operation electrode to an electrical signal line supplying a signal generated in accordance with the electrical acoustic signal, and into the high impedance state by disconnecting the respective operation electrode from both the common ground and the electrical signal line by driving a plurality of switching elements connected to the plurality of operation electrodes. This allows to securely set the desired electrode state by means of a simple and reliable configuration.

The processing portion may further configured to conduct the active grounding procedure for each stimulus being received by the input portion in real time.

The processing portion may comprise at least one processing circuitry, and at least one memory for storing instructions to be executed by the processing circuitry, wherein the at least one memory and the instructions may be configured to, with the at least one processing circuitry, cause the processing portion to conduct the active grounding procedure. The processing circuitry may either part of the implant portion or part of a portion being able to communicate with the implant portion and/or attachable on the outer side of the user. This allows implementation of aspects of the disclosure in different types of hearing devices using a cochlear implant system, wherein the processing portion can be part of the implanted components or of external components. Hence, flexibility of adapting the present disclosure is increased.

The active grounding procedure can also be implement directly into the implant portion configured to be implanted under the skin and on the skull of a user. The active grounding procedure may be hardcoded in the implant portion, e.g. in a memory being part of the implant portion. Additionally, the active grounding procedure may be adjustable.

The active grounding procedure relates to a scheme for grounding each electrodes of the electrode array for obtaining a certain electrical stimulation pattern of the electrodes or to obtain a certain operation mode of the cochlear implant system. The active grounding procedure is controlled by the processing portion.

The high impedance state of an electrode means that the electrode is configured to stimulate with a current.

The grounded state of an electrode means that the electrode is connected to a ground, and the electrode is used as a path for the current to flow from the active electrode.

The high impedance electrode may be an electrode which is either not located within the cochlea and electrode is receiving a stimulation current or the electrode is not receiving a stimulation current. For example, the cochlear implant system includes a switch configuration which is configured to control whether the electrode is in high impedance state, grounded state or in stimulating state. The switch configuration is configured to connect a stimulation current source to an electrode, allowing the electrode to receive a stimulation current. The electrode is in stimulation state. The switch configuration is configured to disconnect the connection between the stimulation current source and the electrode, not allowing the electrode to receive a stimulation current. In this configuration the electrode is in high impedance state. The switch configuration is further configured to connect the electrode to a ground, and in this configuration the electrode is in a grounding state.

The hearing device includes the switch configuration, wherein the switch configuration includes one or more switches configured to connect or disconnect an electrode of the electrode array to either a ground or a stimulation current source. The stimulation current source is implanted into the hearing device.

The switch configuration is not essential for the disclosure as the controlling of the connection to an electrode can be implemented in many different ways.

According to yet another aspect, there is provided a computer program product for a computer, including software code portions for performing the steps of the above defined method when said product is run on the computer. The computer program product may include a computer-readable medium on which said software code portions are stored, and/or the computer program product may be directly loadable into the internal memory of the computer and/or transmittable via a network by means of at least one of upload, download and push procedures.

The user's hearing is not cured with a hearing aid, the improvement in hearing depends only on the hearing aid, and while removing the hearing aid from the user, the user's hearing is either the same or worse. Therefore, none of the disclosed embodiments relates to a treatment of the user's hearing.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 4c illustrates a diagram illustrating an example of an electrode state setting pattern according to an embodiment of the disclosure.

FIG. 4d illustrates a diagram illustrating an example of an electrode state setting pattern according to an embodiment of the disclosure.

FIG. 4e illustrates a diagram illustrating an example of an electrode state setting pattern according to an embodiment of the disclosure.

FIG. 4f illustrates a diagram illustrating an example of an electrode state setting pattern according to an embodiment of the disclosure.

FIG. 4g illustrates a diagram illustrating an example of an electrode state setting pattern according to an embodiment of the disclosure.

FIG. 5 illustrates a flow chart illustrating a control method according to an embodiment of the disclosure.

FIG. 6 illustrates a diagram illustrating a processing portion according to an embodiment of the disclosure.

DETAILED DESCRIPTION

Figure 1:
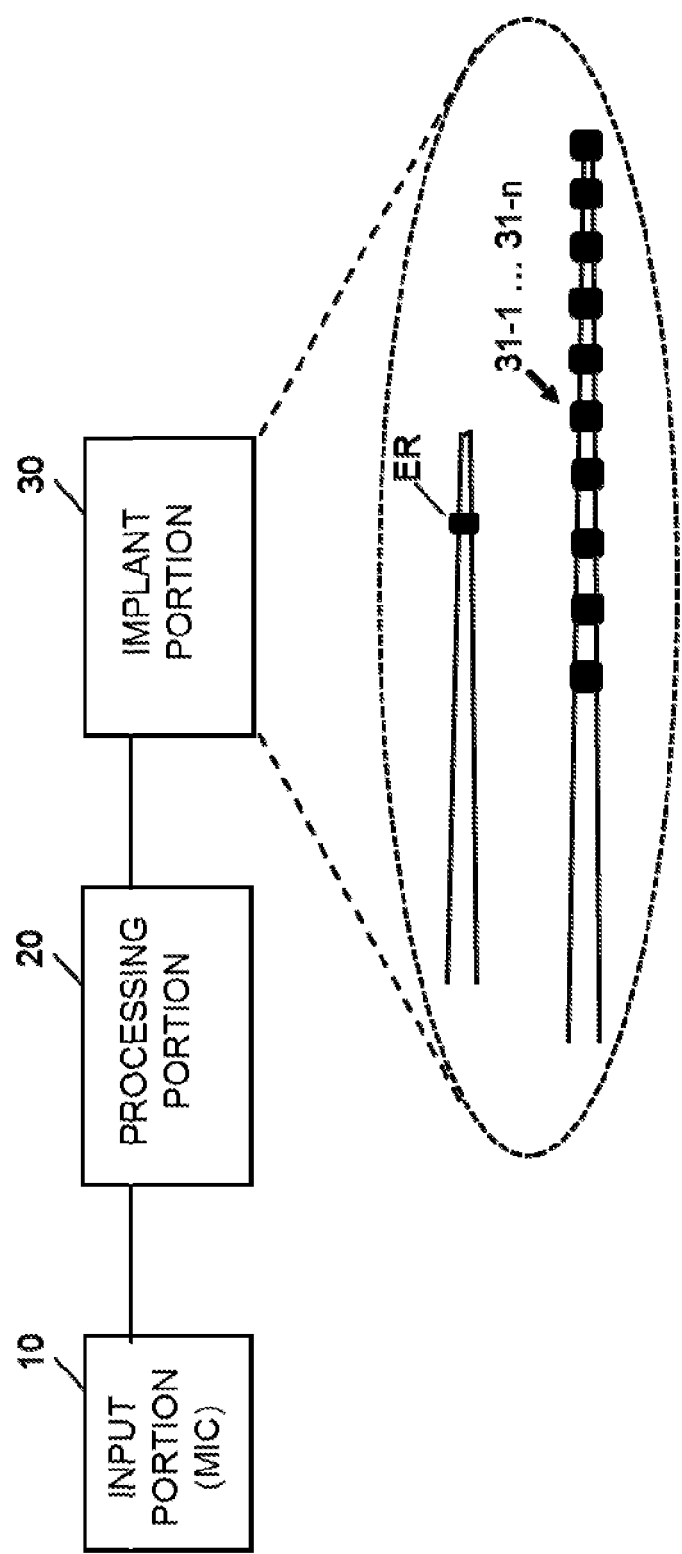
FIG. 1 illustrates a schematic diagram for explaining a basic configuration of a hearing device according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Generally, a hearing device may include a hearing aid that is adapted to improve or augment the hearing capability of a user by receiving an acoustic signal from a user's surroundings, generating a corresponding audio signal, possibly modifying the audio signal and providing the possibly modified audio signal as a signal allowing the user to recognize a sound to at least one of the user's ears.

According to examples of the disclosure, the hearing device may refer to a device such as an earphone or a headset adapted to receive an audio signal electronically, possibly modifying the audio signal and providing the possibly modified audio signals as an audible signal to at least one of the user's ears. Such audible signals may be provided in the form of electric signals transferred directly or indirectly to cochlear nerve and/or to auditory cortex of the user.

At least parts of the hearing device are adapted to be worn in any known way. This may include arranging a unit of the hearing device attached to a fixture implanted into the skull bone such as in Bone Anchored Hearing Aid or Cochlear Implant, or arranging a unit of the hearing device as an entirely or partly implanted unit such as in Bone Anchored Hearing Aid or Cochlear Implant.

A hearing system according to examples of the disclosure refers also to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include one or more output electrodes for providing electric signals such as in a Cochlear Implant.

A cochlear implant system typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

The cochlea is arranged like a rolled-up piano keyboard. Lining the cochlea are many thousands of hair cells that convert the sound into electrical signals. Cochlear implants have a couple of electrodes, each of which performs a similar function to a hair cell or group of hair cells.

Now referring to FIG. 1, which illustrates a schematic diagram for explaining a basic configuration of a hearing device according to an embodiment of the disclosure, the hearing device comprises an input portion or unit 10, such as a microphone or the like, as explained above, a processing portion 20 and an implant portion 30.

The input portion 10 is used to receive acoustic signals which form the basis of a stimulus to be transferred to the user's ear, such as sound or voice. In the input portion 10, the acoustic signal is converted into an electric signal (also referred to as electrical acoustic signal) which is then forwarded to the processing portion 20 for signal processing. The transmission of the electrical acoustic signal to the processing portion 20 is executed, for example, by wired or wireless connections.

The processing portion 20 comprises, for example, a microprocessor, a memory such as a ROM and RAM, and input/output interfaces, or the like. The processing portion 20 receives the electrical acoustic signal from the input portion 10 and conducts a processing. As a result of the processing, control of the implant portion 30 is executed in order to stimulate parts of the cochlea in order to provide the user's ear with a stimulation according to the acoustic signal received by the input portion 10. For example, the processing portion 20 receives from a microphone that detect real time sound signals from the environment and performs a signal processing by using several digital signal processors. After noise reduction, automatic gain control and other pre-processing, the sound signal goes through a filter bank and is decomposed into a series of bandpass-filtered channels (as many as the number of stimulation electrodes, for example).

As illustrated in FIG. 1, the implant portion 30 includes a plurality of electrodes, i.e. an external electrode ER and an array of operation electrodes 31-1 to 31-$n$. The operation electrodes 31-1 to 31-$n$ are disposed, for example, on the carrier as mentioned above which can be inserted into the cochlea of the user. Amongst the operation electrodes, at least one is used for stimulation of the cochlea by using electrical pulses or signals. The number n of operation electrodes is not specifically limited. Examples for a number n of operation electrode may be in the range of 10 to 30, for example. States of the operation electrodes are switchable from grounded state to high impedance state and stimulated state, as explained further below.

The external electrode ER is used as a reference electrode and is grounded, e.g. to a common ground potential like that to which the operation electrodes are switchable. The external electrode is also implementable into the region of the user's ear, but located outside of the cochlea in an area allowing to form an electrical field with the operation electrodes in the cochlea.

It is to be noted that the processing portion 20 can be part of the input portion 10, which is typically located outside of the user. In this case, connection between the processing portion 20 and the input portion 10 is made e.g. by a wired connection, while connection between the processing portion 20 and the implant portion 30 is made by a wireless connection, e.g. by an inductive coupling or the like. On the other hand, the processing portion 20 can be part of the implant portion 30, i.e. part of the elements being located inside the user. In this case, connection between the processing portion 20 and the input portion 10 is made e.g. by a wireless connection, while connection between the processing portion 20 and the implant portion 30 is made by a wired connection.

Figure 2:
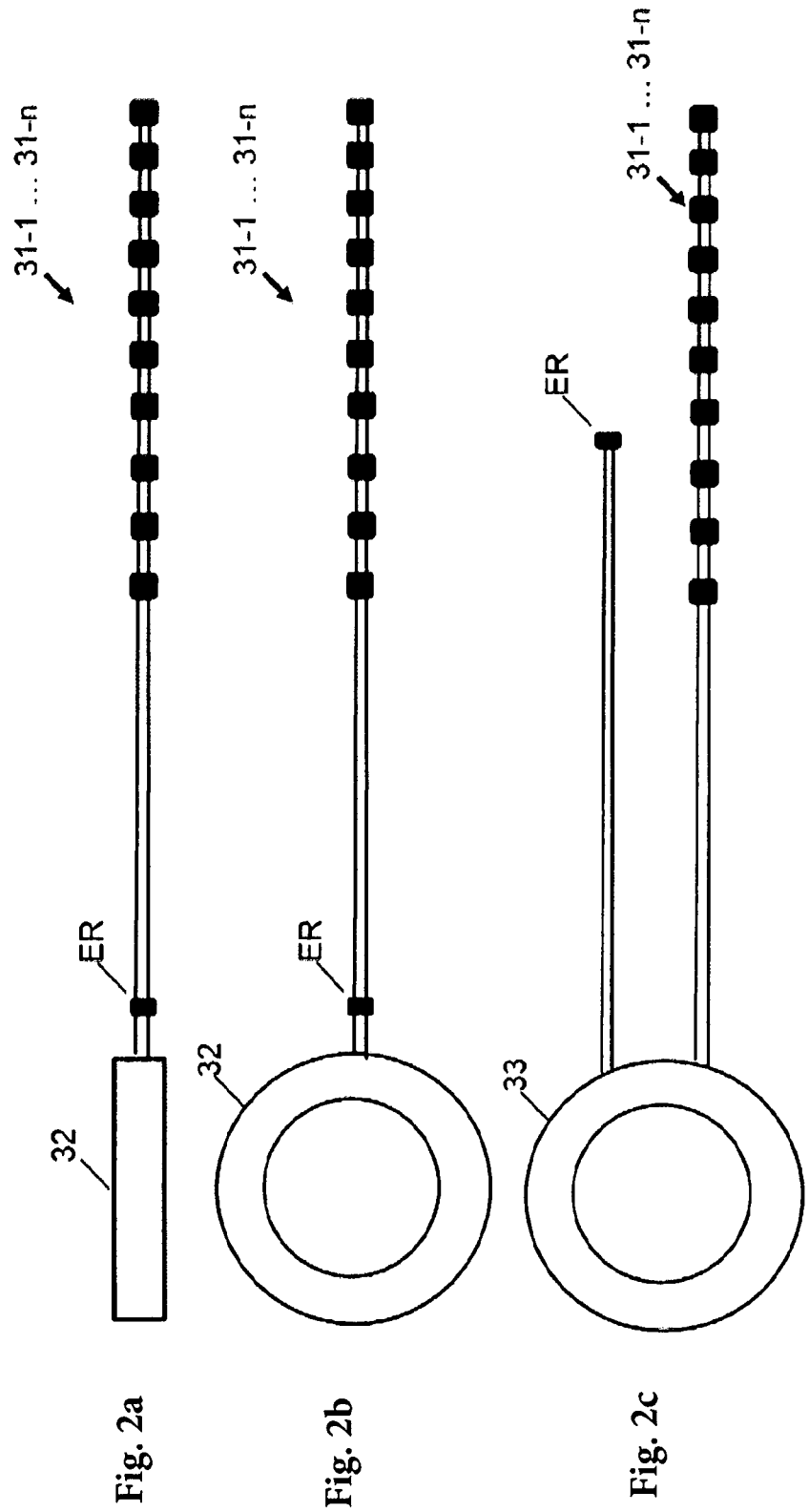
FIG. 2a illustrates a side view of an example of a configuration of an implant portion of a hearing device according to an embodiment of the disclosure.
FIG. 2b illustrates a top view of the example according to FIG. 2a of a configuration of an implant portion of a hearing device according to an embodiment of the disclosure.
FIG. 2c illustrates a top view of another example of a configuration of an implant portion of a hearing device according to an embodiment of the disclosure.

FIGS. 2a to 2c show examples of a configuration of an implant portion 30 of a hearing device according to an embodiment of the disclosure. The implant portion is buried under the scalp during an implantation surgery, for example.

FIG. 2a illustrates a side view of a first example of a configuration of an implant portion 30, while FIG. 2b shows a top view of the same implant portion 30.

Specifically, as shown in FIGS. 2a and 2b, the implant portion 30 has a portion 32 which includes a connection element like an antenna or the like via which the signaling from the input portion 10 (or of the processing portion 20 in case the processing portion is not part of the implant portion) is received. A single carrier extending from the portion 32 includes a reference electrode or external electrode ER and an array of operation electrodes 31-1 to 31-n. The distances of the external electrode ER and the operation electrode 31-1 to 31-n is such that the external electrode can be located outside of the cochlea when the array of the operation electrodes 31-1 to 31-n is (at least partially) inserted into the cochlea. It is to be noted that a pre-set insertion range is set, for example, by means of a corresponding part of the carrier (shown by a triangle in FIGS. 2a and 2b, for example) which defines a stopper or the like prohibiting an excessive insertion of the electrode array, for example.

FIG. 2c illustrates a top view of another example of a configuration of an implant portion of a hearing device according to an embodiment of the disclosure. Specifically, as shown in FIG. 2c, the implant portion 30 has a portion 33 which includes, similarly to the configuration according to FIGS. 2a/b, a connection element like an antenna or the like via which the signaling from the input portion 10 (or of the processing portion 20 in case the processing portion is not part of the implant portion) is received. However, instead of a single carrier like in the example shown in FIGS. 2a/b, the example shown in FIG. 2c comprises two carriers extending from the portion 33, one of which includes a reference electrode or external electrode ER and the other includes an array of operation electrodes 31-1 to 31-n.

It is to be noted that the reference electrode can by any kind of an electrode positioned outside the cochlea.

Figure 3:
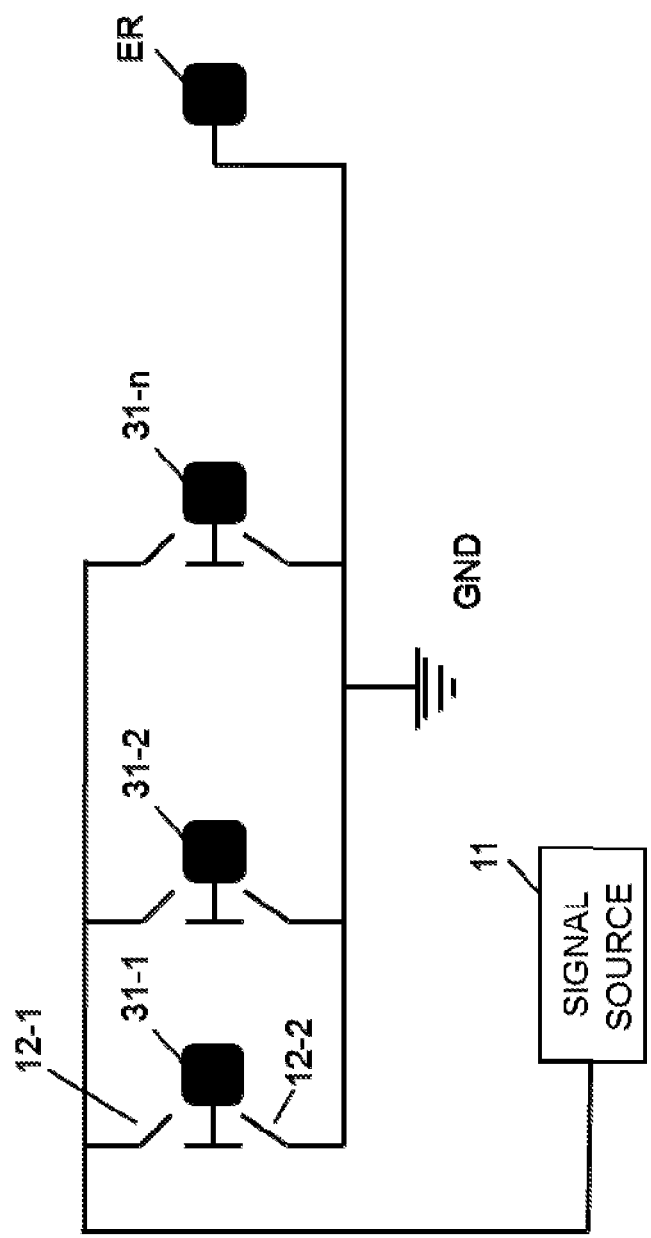
FIG. 3 illustrates a schematic circuit diagram of electrodes arranged in an implant portion of a hearing device according to an embodiment of the disclosure.

FIG. 3 illustrates a schematic circuit diagram of electrodes arranged in an implant portion of a hearing device according to an embodiment of the disclosure. Specifically, FIG. 3 illustrates, in a simplified manner, a principle configuration allowing to drive the operation electrodes 31-1 to 31-n, i.e. to set the operation electrodes 31-1 to 31-n into one of a grounded state (i.e. a state in which they are connected to a ground potential, e.g. the potential of the reference electrode ER), a high impedance state and a stimulated state in which the electrode is connected to a signal source providing a stimulus (i.e. a signal according to the electrical acoustic signal which is to be sensed by the user).

As shown in FIG. 3, the respective operation electrodes 31-1 to 31-n are each connected to two switching elements 12-1, 12-2. For example, the switching elements are formed by transistors or the like allowing to open and close a connection to a conducting line. One of the switching elements, i.e. elements 12-1, connect the respective operation electrode 31-1 to 31-n to a signal source 11, which provides a signal according to the electrical acoustic signal used for stimulating the user's ear. The other of the switching elements, i.e. elements 12-2, connect to ground GND.

Also indicated in FIG. 3 is the external (reference) electrode ER which is connected to ground GND permanently.

The switching elements 12-1 and 12-2 are individually controlled by the processing portion 30, for example. That is, the respective switching element 12-1 and 12-2 can be switched in the on state (connected state) or off state (disconnected state) for changing the state of the electrodes 31-1 to 31-n according to an electrode state setting patterns determined in the processing portion 30 (to be described later).

Specifically, when the switching element 12-1 is in the on state while the switching element 12-2 is in the off state, the corresponding electrode is connected to the signal source, which leads to a stimulated state of this electrode. On the other hand, in case the switching element 12-2 is in the on state while switching element 12-1 is in the off state, the corresponding electrode is connected to ground, which lead to a grounded state of this electrode. In case both the switching element 12-2 and the switching element 12-1 are in the off state, the corresponding electrode is disconnected, which lead to a high impedance state of this electrode.

It is to be noted that the example presented in FIG. 3 is only for illustrative purposes, and other ways for achieving a designated electrode state are possible.

As described above, one problem to be faced in connection with cochlear implant systems is that an electrical field generated during the activation of any electrode widely spread into the cochlea, resulting in broad and unfocused excitations of the auditory nerve fibers.

In order to handle this problem, electrode states (i.e. an active or stimulated state, a grounded state and a high impedance state) are to be properly controlled so as to steer the electrical excitatory centre and to control the spread of excitation.

Cochlear implant systems are able to set the internal connection topology and the current intensity independently on each electrode. In order to achieve a desired current pattern with limited number of electrodes in the cochlea, the proportion of current on each electrode in a single stimulus is carefully controlled, resulting in different stimulation modes.

A commonly used stimulation mode in cochlear implant system is called monopolar mode. Here, one electrode is being activated (i.e. stimulus is supplied), while one is grounded and all other electrodes are put in a high impedance state. Because the grounded electrode is implanted outside the cochlea, the returning path is long-distance and spatial spread of the current is maximal. Hence, the stimulation current tends to penetrate deeper into the tissue, which gives monopolar mode a high stimulation efficiency, meaning that it can reach the same neural activation level with lower current level. However, the long distance between the two poles of stimulation also leads to wide current spread, which reduces the spatial selectivity of this stimulation mode.

One possibility to reduce the spread of excitation is using intracochlear electrodes to return the current. This return can be completely done with intracochlear electrodes (corresponding modes are e.g. bipolar, tripolar, common ground, which will be explained below), or a trade-off between intracochlear and extracochlear electrodes is used (this is referred to as multi-mode grounding to be explained below).

Bipolar and common ground are two examples of stimulation modes that use the non-stimulating intracochlear electrodes as return electrodes. In bipolar stimulation, one of the neighbors of the stimulating electrode is used as the return electrode, which receives the same amount of current send by the stimulating electrode. The separation between the stimulating and returning electrodes can also be increased to make a trade off between spatial selectivity and stimulation efficiency, leading to a so-called BP+n stimulation, where n is the number of unused electrodes between the stimulating and returning electrodes.

However, modes like the bipolar stimulation has an asymmetrical current distribution as the returning electrode can only be on one side of the stimulating electrode. Therefore, tripolar stimulation is used which mitigates this problem by employing both neighbors as returning electrodes, each receiving e.g. 50% of the stimulation current.

A further development of the tripolar stimulation leads to a current steering strategy, which aims at activating the auditory nerve fibers that lie in the gaps between the intracochlear electrodes. Current steering can create virtual stimulation channels between neighboring electrodes, resulting in increased pitch perception by the recipients. It is implemented e.g. by making an imbalanced current return path: the ratio of the returning current taken by one neighbor of the stimulating electrode is $\alpha\sigma$, while the ratio for the other neighbor is $(1-\alpha)\sigma$, where $\sigma$ is the same compensation coefficient as in the partial tripolar and $\alpha$ is the steering coefficient ($0 \leq \alpha \leq 1$). The proportion of current that returns to the reference electrode is still $(1-\sigma)$.

Common ground is an attempt of focusing the stimulation current. It uses all the non-stimulating intracochlear electrodes as return electrodes. Since the return current is more distributed, the chances of unnecessary neural activation caused by the negative peak of electric potential on the returning electrodes can be reduced. Unlike bipolar or tripolar stimulations, the returning electrodes in this mode are passive, which means they are directly connected to the ground of the stimulation current source, hence the name "common ground".

In multi-mode grounding stimulation mode, on the other hand, beside the non-stimulating intracochlear electrodes, this mode also allows current to return through the reference electrode. Since the surface area of the reference electrode can be made much larger than the intracochlear electrodes, it provides a low impedance path for the current, which may compensate for the increased impedance at the base and apex in common ground mode. The multi-mode grounding represents a compromise that can take the benefits from both the monopolar (efficiency) and common ground (focused) modes.

One difficulty faced in neural stimulations is avoiding any tissue damage coming from Faradaic reactions. To do so, the generation of any electrical charge in the tissue is quasi immediately compensated by the injection of a current opposite in charge. This can be easily achieved in the monopolar stimulation mode where the balance is simply achieved by reversing the order of the activated and grounded electrodes. In the multi-mode grounding, however, the complexity of the returning path makes active balances difficult to achieve.

Even though not shown in FIG. 3, capacitors can be connected in series to each operation electrode contact. This allows to balance current by grounding all other electrodes and passively discharge them immediately thereafter. However, in case the electrode grounding state is not controlled (i.e. always grounded), there may be problems regarding electrical stimulations. For example, problems arise in case of partial insertion of the electrode array in the cochlea. Furthermore, there may be no control over the returning path nor the electrical spread.

It is contemplated to deal with this problems by controlling the grounded channels independently. According to examples of embodiments of the disclosure, measures for determining an active grounding procedure are proposed which is adaptable in real time for each stimulus. That is, according to the disclosure, the stimulation can be performed between a stimulated electrode and one or more others electrodes and/or the external electrode (reference electrode).

According to examples of embodiments of the disclosure, it is possible to implement a corresponding active grounding procedure permanently, i.e. in a fixed manner, or a flexible and adaptice control process can be implemented, e.g. based on a real time monitoring of various properties and conditions, so as to determine and employ varying electrode state setting patterns for the operation electrodes, depending e.g. on an implantation state of the operation electrodes (e.g. partially inserted or fully inserted in the cochlea), a functional state of the operation electrodes (e.g. a defect in one or more of the electrodes), a sound strategy (e.g. a property of an input acoustic electrical signal, such as music or voice) or the like.

It is to be noted that an adaptive grounding strategy according to examples of embodiments of the disclosure does not require a high energy consumption since is corresponds to the management of several connection switches to a reference potential. Therefore, examples of embodiments of the disclosure can be used in an approach for a ultra-low power stimulator since it can be associated to a passive discharge strategy.

For example, one or more of the following operation modes for an adaptive grounding control according to examples of embodiments of the disclosure are applicable.

A safety mode is implemented, for example, in case of a partial insertion of the electrode array comprising the operation electrodes. In this case, extracochlear electrodes being not inserted are systematically switched to a high impedance state.

A focused mode is related to a case where the adjacent electrodes on each side of the stimulated electrode (i.e. the two closest electrodes, the four closest electrodes etc. flanking the stimulated electrode) are grounded, like the reference electrode.

A steering mode is related to a case where asymmetric gradients of impedances are created inside the cochlea by switching a number of electrodes on one side of the stimulated electrode to passive ground. The shape of the current flow is thereby modulated so that it is possible to selectively direct the current to a specific region of the cochlea.

A passive full-monopolar mode is implemented for setting using only the passive external grounded electrode.

Details regarding the above described modes are explained in the following with reference to FIGS. 4a to 4g.

Basically, each of FIGS. 4a to 4g shows a state where an implant portion of the hearing device according to examples of embodiments of the disclosure is implanted in the user's skull with the electrode array comprising the operation electrodes 31-a to 31-n being (at least partially) inserted into the user's cochlea while the reference electrode portion comprising the (grounded) external electrode ER being located outside of the cochlea. The cochlea 61 (shown by a dashed structure) is illustrated in an unrolled configuration for the sake of simplicity of the illustration. The carrier with the electrodes 31-1 to 31-n is shown in an inserted state within the cochlea 61. It is to be noted that the base of the cochlea 61 (on the left side in the FIGS. 4a to 4g), which is where the electrode array enters, responds to the highest pitches. The apex, or innermost part of the cochlea 61 (shown on the right side in the FIGS. 4a to 4g) responds to the low-frequency tones. The locations in between the base and the apex correspond to the range of frequencies in between the two extremes.

Furthermore, in FIGS. 4a to 4g, a current distribution between the stimulated electrode (indicated in the Figures by an arrow in the upward direction located at one electrode of the operation electrodes 31-1 to 31-n) and other electrodes one connected to the reference voltage (GND, indicated in FIGS. 4a to 4g by arrows in the downward direction) is indicated by circle 51 (towards the external electrode ER) and circle 52 (with operation electrodes being grounded). A part of the cochlea which will be excited is indicated by a black line 62.

It is to be noted that each stimulation electrode 31-1 to 31-n is connected to a capacitor (not shown) so that in case an operation electrode is grounded the capacitor is passively discharged.

Figure 4A:
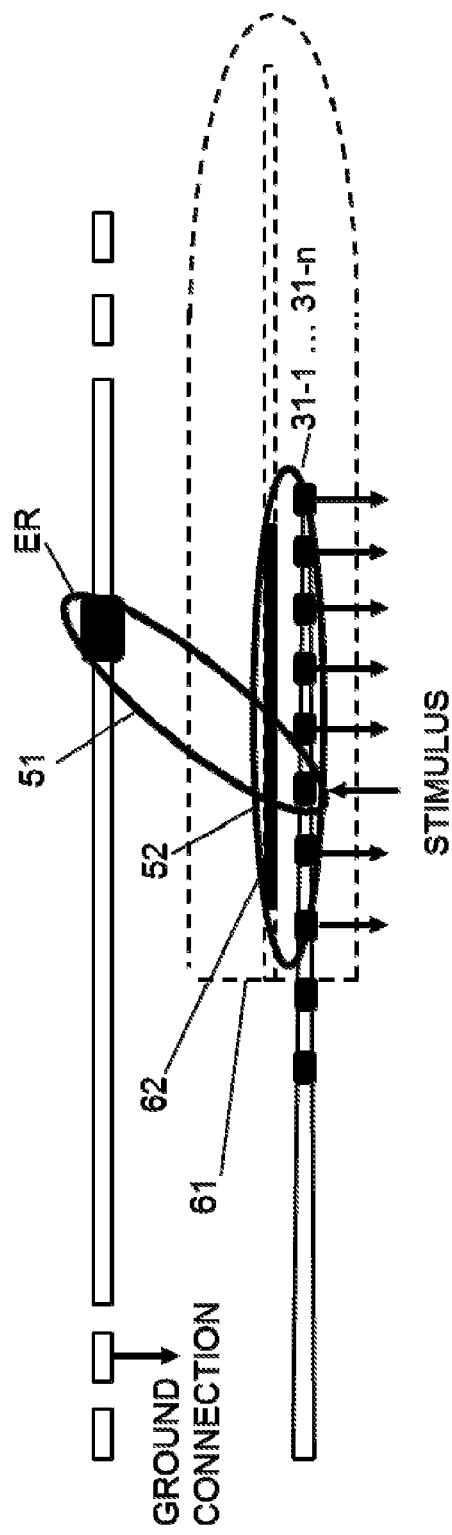
FIG. 4a illustrates a diagram illustrating an example of an electrode state setting pattern according to an embodiment of the disclosure.

FIG. 4a illustrates a diagram illustrating an example of an electrode state setting pattern according to an embodiment of the disclosure which is implemented in the above described safety mode. When the cochlear implantation is partial, electrical stimulations may pass through the cochlear wall even if the extracochlear electrodes (the electrodes on the left side being outside the cochlea 61) are deactivated. Therefore, these extracochlear electrodes have to be both deactivated and put in a high impedance state. This configuration ensure than no current will pass through the unimplanted electrode array area. In other words, the operation electrodes which are outside the cochlea are set to high impedance state in order to avoid any unwanted stimulation/excitation of nerve cells within the cochlea.

Figure 4B:
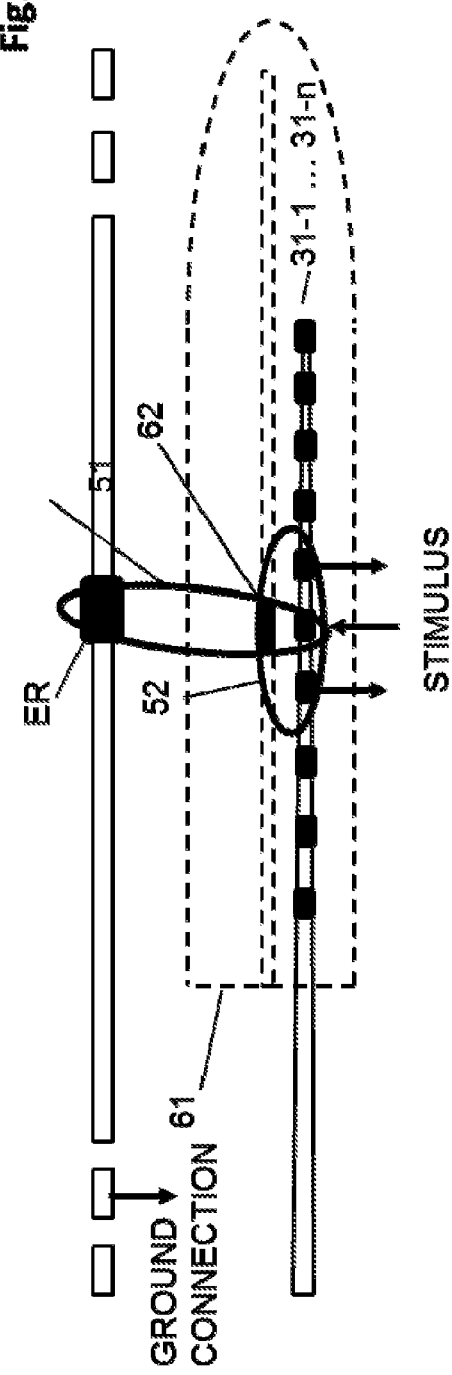
FIG. 4b illustrates a diagram illustrating an example of an electrode state setting pattern according to an embodiment of the disclosure.

FIGS. 4b and 4c illustrate diagrams illustrating an example of an electrode state setting pattern according to an embodiment of the disclosure which is implemented in the above described focused mode. In FIG. 4b, a case is shown where the closest electrode on each side of the stimulated electrode (i.e. two electrodes) is put to the grounded state and used to passively discharge the current. All of the other operation electrodes are left in a high impedance state. Due to this, the electrical current can be focused on a specific part of the cochlea. On the other hand, FIG. 4c shows a case where the number of electrodes put in the grounded state is increased (i.e. four neighboring electrodes). In this case the current can be further reduced. That is, when the number of grounded neighboring electrodes is increased, a narrower part of the cochlea is excited. Thus, for example, cross talk between the electrodes can be reduced.

By providing a symmetrical grounding procedure of operation electrodes being adjacent to the stimulated electrode, as depicted in FIGS. 4b and 4c, it is possible to focus the stimulation of nerve cells because the width of the current field flowing between the stimulus electrode and the reference electrode ER is narrowed. A larger number of neighbouring fields results in a more focused current field (smaller area of the cochlea is stimulated) but on the other hand the intensity of the current flowing to the reference electrode ER is reduced because more of the current is flowing within the cochlea.

FIGS. 4d, 4e and 4f illustrate diagrams illustrating an example of an electrode state setting pattern according to an embodiment of the disclosure which is implemented in the above described steering mode. Here, the grounding state of operation electrodes is asymmetrically set and used to control the current flow in a desired direction. Due to this, the electrical field can be steered, or a virtual electrode is generated allowing to reach further parts of the cochlea. That is, an asymmetrical grounding of the operation electrodes allows, for example, to generate a virtual electrode reaching parts of the cochlea not being covered by the electrode array, or to stimulate an area of the cochlea where e.g. one or more of the operation electrodes are defect or broken.

FIGS. 4d and 4e are related to an electrode setting pattern used for steering. That is, the electrical field of excitation center is changed by controlling the grounded or high impedance states of operation electrodes. It is to be noted that basically it is possible that only one of the operation electrodes is grounded in this mode. However, according to the examples shown in FIGS. 4d and 4e, two or more of the operation electrodes are grounded. When comparing the illustrations of FIGS. 4d and 4e, the higher the number of grounded electrodes, the larger the area of the cochlea being excited.

As indicated above, the steering mode is applicable, for example, in case where an operation electrode is defect. In this situation, when using the steering mode, where an asymmetrical grounding of the operation electrodes is effected in respect to the stimulated electrode, the cochlea area corresponding to the defect electrode can still be stimulated. For example, assuming a case where an operation electrode between the stimulated electrode and a group of grounded operation electrodes is broken. Then, in the steering mode shown in FIGS. 4d and 4e, the current flows from the stimulated electrode to the reference electrode, and a broader excitation of the cochlea (region 62) is provided because the current flowing within the cochlea starts from the stimulus electrode and stretches across the defect electrode and towards the group of grounded stimulation electrodes.

FIG. 4f is related to a generation of a virtual electrode. The virtual electrode is generated from the end of the electrode array (i.e. the last of the operation electrodes 31-n) towards the apex of the cochlea, wherein an assumed margin of the virtual electrode is illustrated in FIG. 4f by a dotted line. For achieving the virtual electrode, setting of the operation electrodes 31-1 to 31-n into the grounded state and the high impedance state is driven so that the current is steered in the apex in a region that is not physically covered by the operation electrodes of the electrode array. This is achieved by an asymmetric grounding procedure close to the dedicated zone.

The virtual electrode is useful since of mechanical issues it is not possible to insert the implant portion fully into the low pitch portion of the cochlea. Therefore, it is advantageous to generate a virtual electrode in continuation of the operation electrodes, because then it is possible to excite/stimulate further into the cochlea without placing an actual stimulation electrode. The virtual electrode is generated because of a high current field generated at the end of the plurality of the operation electrodes. The high current field is generated because of a high number of grounded operation electrodes on the one side of the stimulated electrode.

FIG. 4g illustrates a diagram illustrating an example of an electrode state setting pattern according to an embodiment of the disclosure which is implemented in the above described passive full-monopolar mode. Here, the returning current is being driven by the grounded reference electrode ER which is passively discharging the current opposing its charge. An active balancing is not conducted.

FIG. 5 illustrates a flow chart illustrating a control method according to an embodiment of the disclosure. Specifically, FIG. 5 describes a control method for a hearing device for use in a cochlear implant system according to examples of embodiments of the disclosure. The hearing device is based, for example, on a configuration as described in connection with FIGS. 1 to 3. That is, the control method is usable in a the hearing device comprising an input portion such as the input unit 10 configured to receive, as a stimulus, an acoustic signal, to convert the acoustic signal into an electrical acoustic signal and to provide the electrical acoustic signal, a processing portion configured to process the electrical acoustic signal and to conduct an active grounding procedure, an implant portion configured to be implantable at least partially in a cochlea of the user and comprising a plurality of operation electrodes for electrically stimulating different frequency ranges, and a reference electrode part including at least one external electrode being grounded and implantable outside of the cochlea of the user.

According to the control method, the plurality of operation electrodes are driven by the processing portion on the basis of the electric acoustic signal.

According to examples of embodiments of the disclosure, in S100, the electrical acoustic signal coming from the input portion 10 such as a microphone is processed.

Then, in S110, an active grounding procedure is executed which is based on the measures described, for example, in connection with FIGS. 4a to 4g. For example, the active grounding procedure is conducted for each stimulus being received by the input portion in real time.

Specifically, in S120, an electrode state setting pattern for selecting, according to an operation mode of the cochlear implant system, one of a plurality of electrode state setting patterns is determined. Each of the electrode state setting patterns is adapted to enable a stimulation by a stimulation electrode of the plurality of operation electrodes being in a stimulating state, wherein at least one of the plurality of operation electrodes is in a grounded state or in a high impedance state.

For example, according to some examples of embodiments of the disclosure, a determination is made regarding an operation mode in which the cochlear implant system currently is or an estimation is made regarding an operation mode in which the cochlear implant system is going to be in a predetermined time period. For example, the determination regarding the present or a future operation mode is made on the basis of measurement results of environmental conditions (including the kind of sound to be processed for the electrical acoustic signal, such as a frequency range or the like), a condition of the implant system (for example, is the implant portion completely or partially inserted into the cochlea, is there a failure of any of the operation electrodes, is a configuration setting of the hearing device to be considered, and the like). In other words, a processing for the determination of the operation mode considers at least one parameter of a property of an input electrical acoustic signal, an implantation state of the plurality of operation electrodes, a functional state of each of the plurality of operation electrodes, an instruction input into a configuration setting, and an entering into a low power operation mode.

According to examples of embodiments of the disclosure, the operation mode of the cochlear implant system comprises at least one of a safety mode (see also FIG. 4a) related to a situation where, of the plurality of operation electrodes, only a part is inserted into the cochlea, wherein the electrodes being not inserted are set into a high impedance state. Another operation mode is a focused mode (see FIGS. 4b and 4c) related to a situation where a current flow is to be focused on a specific part of the cochlea using a symmetrical setting of operation electrodes into the grounded state. Another mode is a steering mode (see FIGS. 4d and 4e) related to a situation where a current flow is to be directed to a specific part of the cochlea by steering an electrical field using an asymmetrical setting of operation electrodes into the grounded state. In this context, also a virtual electrode mode (see FIG. 4f) is to be seen which is related to a situation where a current flow is to be directed to a part of the cochlea not overlapping the implant portion using an asymmetrical setting of operation electrodes into the grounded state. Moreover, a passive full-monopolar mode (see FIG. 4g) is provided which is related to a situation where a current flow is to be passively discharged.

Specifically, according to examples of embodiments of the disclosure, the selected electrode state setting pattern is based on the following:

- in case the operation mode of the cochlear implant system is the safety mode, an electrode state setting pattern is selected causing to set at least one of the plurality of operation electrodes into the stimulated state according to the electrical acoustic signal, and to set all electrodes of the plurality of operation electrodes being located outside the cochlea into the high impedance state;
- in case the operation mode of the cochlear implant system is the focused mode, an electrode state setting pattern is selected causing to set at least one of the plurality of operation electrodes into the stimulated state according to the electrical acoustic signal, to symmetrically set at least two of the plurality of operation electrodes being adjacent to the stimulated electrode into the grounded state, and to set the remaining electrodes of the plurality of operation electrodes into the high impedance state;
- in case the operation mode of the cochlear implant system is the steering mode, an electrode state setting pattern is selected causing to set at least one of the plurality of operation electrodes into the stimulated state according to the electrical acoustic signal, to asymmetrically set at least two of the plurality of operation electrodes being located on one side of the stimulated electrode into the grounded state, and to set the remaining electrodes of the plurality of operation electrodes into the high impedance state;
- in case the operation mode of the cochlear implant system is the virtual electrode mode, an electrode state setting pattern is selected causing to set at least one of the plurality of operation electrodes into the stimulated state according to the electrical acoustic signal, to set each electrode of the plurality of operation electrodes being located on one side of the stimulated electrode towards the distal end of the implant portion into the grounded state, and to set the electrodes of the plurality of operation electrodes being located on the other side of the stimulated electrode into the high impedance state; and
- in case the operation mode of the cochlear implant system is the passive full-monopolar mode, an electrode state setting pattern is selected causing to set at least one of the plurality of operation electrodes into the stimulated state according to the electrical acoustic signal, and to set the remaining electrodes of the plurality of operation electrodes into the high impedance state.

In S130, according to the selected electrode state setting pattern of S120, the plurality of operation electrodes are set into a specified electrode state of a high impedance state, a grounded state and a stimulating state in which a signal based on the electric acoustic signal is supplied to a stimulation electrode of the plurality of operation electrodes.

For example, according to examples of embodiments of the disclosure, the plurality of operation electrodes are set into the grounded state by causing connecting the respective operation electrode to a common ground of the hearing device, into the stimulating state by connecting the respective operation electrode to an electrical signal line supplying a signal generated in accordance with the electrical acoustic signal, and into the high impedance state by disconnecting the respective operation electrode from both the common ground and the electrical signal line. These settings are achieved, for example, by driving a plurality of switching elements (such as transistors) connected to the plurality of operation electrodes between on and off states.

FIG. 6 illustrates a diagram illustrating a processing portion according to an embodiment of the disclosure. Specifically, FIG. 6 shows a diagram of an element or device acting as a processing portion according to some examples of embodiments of the disclosure, i.e. the processing portion 20 of FIG. 1, which is configured to conduct a control procedure including the active grounding procedure according to examples of embodiments of the disclosure. It is to be noted that the processing portion 20 of FIG. 1 may include further elements or functions besides those described herein below. Furthermore, even though reference is made to a element or function acting as a processing portion, the element or function may be also another device or function having a similar task, such as a chipset, a chip, a module, an application etc., which can also be part of a processing portion of a hearing device or attached as a separate element to a corresponding hearing device, or the like. It should be understood that each block and any combination thereof may be implemented by various means or their combinations, such as hardware, software, firmware, one or more processors and/or circuitry.

The processing portion 20 shown in FIG. 6 may include a processing circuitry, a processing function, a control unit or a processor 201, such as a CPU or the like, which is suitable for executing instructions given by programs or the like related to the control procedure. The processor 201 may include one or more processing portions or functions dedicated to specific processing as described below, or the processing may be run in a single processor or processing function. Portions for executing such specific processing may be also provided as discrete elements or within one or more further processors, processing functions or processing portions, such as in one physical processor like a CPU or in one or more physical or virtual entities, for example. Reference sign 202 and 203 denote input/output (I/O) units or functions (interfaces) connected to the processor or processing function 201. The I/O unit 202 may be used for communicating with the input portion 10, as described in connection with FIG. 1, for example. The I/O units 203 may be used for communicating with the operation electrodes, i.e. with the switching elements 12-1, 12-2, for example, for setting the electrodes 31-1 to 31-$n$ into the desired state. The I/O units 203 may be a combined unit including links towards several elements, or may include a distributed structure with a plurality of different interfaces for different elements. Reference sign 204 denotes a memory usable, for example, for storing data and programs to be executed by the processor or processing function 201 and/or as a working storage of the processor or processing function 201. It is to be noted that the memory 204 may be implemented by using one or more memory portions of the same or different type of memory.

The processor or processing function 201 is configured to execute processing related to the above described control processing. In particular, the processor or processing circuitry or function 201 includes one or more of the following sub-portions. Sub-portion 2011 is a processing portion which is usable as a portion for processing the electrical acoustic signal from the input portion. The portion 2011 may be configured to perform processing according to S100 of FIG. 5. Furthermore, the processor or processing circuitry or function 201 may include a sub-portion 2012 usable as a portion for determining an electrode state setting pattern. The portion 2012 may be configured to perform a processing according to S110 and S120 of FIG. 5. In addition, the processor or processing circuitry or function 201 may include a sub-portion 2013 usable as a portion for setting an electrode state. The portion 2013 may be configured to perform a processing according to S130 of FIG. 5.

It is to be noted that according to one aspect, the functions described above, in particular with regard to the measures described in connection with FIG. 5, may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In an further aspect, a data processing system comprising a processor adapted to execute the computer program for causing the processor to perform at least some (such as a majority or all) of the steps of the method described above and in the claims is provided. The data processing system comprises, for example, a processor as described in connection with FIG. 6.

It is intended that the structural features of the devices described above, either in the detailed description and/or in the claims, may be combined with steps of the method, when appropriately substituted by a corresponding process.

As used above, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing device for use with a cochlear implant system configured to improve or augment a hearing capability of a user, comprising
an input portion configured to receive, as a stimulus, an acoustic signal, and to convert the acoustic signal into an electrical acoustic signal,
a processing portion configured to obtain the electrical acoustic signal from the input portion, to process the electrical acoustic signal and to conduct an active grounding procedure to determine an operation mode of the cochlear implant system,
an implant portion configured to be implantable at least partially in a cochlea of the user and comprising a plurality of operation electrodes for electrically stimulating different frequency ranges, and a reference electrode part including at least one external electrode being grounded and implantable outside of the cochlea of the user, wherein the plurality of operation electrodes are driven by the processing portion on the basis of the electric acoustic signal,
wherein the processing portion further comprises
an electrode state setting section configured to set the plurality of operation electrodes into one of a high impedance state, a grounded state and a stimulating state in which a signal based on the electric acoustic signal is supplied to a stimulation electrode of the plurality of operation electrodes, and
an electrode state setting pattern determining section configured to select, according to the operation mode of the cochlear implant system, one of a plurality of electrode state setting patterns, wherein each of the electrode state setting patterns is adapted to enable a stimulation by a stimulation electrode of the plurality of operation electrodes being in a stimulating state and at least one of the plurality of operation electrodes being in a grounded state or in a high impedance state,
wherein the stimulating state is defined as a state in which an operation electrode is configured to stimulate with a current,
wherein the grounded state is defined as a state in which an operation electrode is connected to a ground and used as a path for the current to flow from the stimulation electrode, and
wherein the electrode state setting section is further configured to cause setting of the plurality of operation electrodes into a specified electrode state of the high impedance state, the grounded state and the stimulating state according to the selected electrode state setting pattern.

2. The hearing device according to claim 1,
wherein the processing portion further comprises an operation mode determining portion configured to determine in which operation mode the cochlear implant system currently is or to estimate in which operation mode the cochlear implant system is going to be in a predetermined time period,
wherein a processing for the determination of the operation mode considers at least one parameter of
a property of an input electrical acoustic signal,
an implantation state of the plurality of operation electrodes,
a functional state of each of the plurality of operation electrodes,
an instruction input into a configuration setting, and
an entering into a low power operation mode.

3. The hearing device according to claim 2, wherein the electrode state setting section is configured to cause setting of the plurality of operation electrodes into
the grounded state by causing connecting the respective operation electrode to a common ground of the hearing device,
into the stimulating state by connecting the respective operation electrode to an electrical signal line supplying a signal generated in accordance with the electrical acoustic signal, and
into the high impedance state by disconnecting the respective operation electrode from both the common ground and the electrical signal line
by driving a plurality of switching elements connected to the plurality of operation electrodes.

4. The hearing device according to claim 2, wherein the processing portion is further configured to conduct the active grounding procedure for each stimulus being received by the input portion in real time.

5. The hearing device according to claim 1, wherein the electrode state setting pattern determining section is configured to select as an electrode state setting pattern at least one of:
in case the operation mode of the cochlear implant system is a safety mode, an electrode state setting pattern causing to set at least one of the plurality of operation electrodes into the stimulated state according to the electrical acoustic signal, and to set all electrodes of the plurality of operation electrodes being located outside the cochlea into the high impedance state,
in case the operation mode of the cochlear implant system is a focused mode, an electrode state setting pattern causing to set at least one of the plurality of operation electrodes into the stimulated state according to the electrical acoustic signal, to symmetrically set at least two of the plurality of operation electrodes being adjacent to the stimulated electrode into the grounded state, and to set the remaining electrodes of the plurality of operation electrodes into the high impedance state,
in case the operation mode of the cochlear implant system is a steering mode, an electrode state setting pattern causing to set at least one of the plurality of operation electrodes into the stimulated state according to the electrical acoustic signal, to asymmetrically set at least two of the plurality of operation electrodes being located on one side of the stimulated electrode into the grounded state, and to set the remaining electrodes of the plurality of operation electrodes into the high impedance state, in case the operation mode of the cochlear implant system is a virtual electrode mode, an electrode state setting pattern causing to set at least one of the plurality of operation electrodes into the stimulated state according to the electrical acoustic signal, to set each electrode of the plurality of operation electrodes being located on one side of the stimulated electrode towards the distal end of the implant portion into the grounded state, and to set the electrodes of the plurality of operation electrodes being located on the other side of the stimulated electrode into the high impedance state, in case the operation mode of the cochlear implant system is a passive full-monopolar mode, an electrode state setting pattern causing to set at least one of the plurality of operation electrodes into the stimulated state according to the electrical acoustic signal, and to set the remaining electrodes of the plurality of operation electrodes into the high impedance state.

6. The hearing device according to claim 5, wherein
the electrode state setting section is configured to cause
setting of the plurality of operation electrodes into
the grounded state by causing connecting the respective operation electrode to a common ground of the hearing device,
into the stimulating state by connecting the respective operation electrode to an electrical signal line supplying a signal generated in accordance with the electrical acoustic signal, and
into the high impedance state by disconnecting the respective operation electrode from both the common ground and the electrical signal line
by driving a plurality of switching elements connected to the plurality of operation electrodes.

7. The hearing device according to claim 1, wherein
the electrode state setting section is configured to cause
setting of the plurality of operation electrodes into
the grounded state by causing connecting the respective operation electrode to a common ground of the hearing device,
into the stimulating state by connecting the respective operation electrode to an electrical signal line supplying a signal generated in accordance with the electrical acoustic signal, and
into the high impedance state by disconnecting the respective operation electrode from both the common ground and the electrical signal line by driving a plurality of switching elements connected to the plurality of operation electrodes.

8. The hearing device according to claim 7, wherein
the electrode state setting section is configured to cause
setting of the plurality of operation electrodes into
the grounded state by causing connecting the respective operation electrode to a common ground of the hearing device,
into the stimulating state by connecting the respective operation electrode to an electrical signal line supplying a signal generated in accordance with the electrical acoustic signal, and
into the high impedance state by disconnecting the respective operation electrode from both the common ground and the electrical signal line
by driving a plurality of switching elements connected to the plurality of operation electrodes.

9. The hearing device according to claim 1, wherein the processing portion is further configured to conduct the active grounding procedure for each stimulus being received by the input portion in real time.

10. The hearing device according to claim 1, wherein the processing portion comprises at least one processing circuitry, and at least one memory for storing instructions to be executed by the processing circuitry, wherein the at least one memory and the instructions are configured to, with the at least one processing circuitry, cause the processing portion to conduct the active grounding procedure, wherein the processing circuitry is either part of the implant portion or part of a portion being able to communicate with the implant portion and attachable on the outer side of the user.

11. A control method for a hearing device for use in a cochlear implant system configured to improve or augment a hearing capability of a user, wherein the hearing device comprises an input portion configured to receive, as a stimulus, an acoustic signal, and to convert the acoustic signal into an electrical acoustic signal, a processing portion configured to obtain the electrical acoustical signal from the input portion, to process the electrical acoustic signal and to conduct an active grounding procedure to determine an operation mode of the cochlear implant system, an implant portion configured to be implantable at least partially in a cochlea of the user and comprising a plurality of operation electrodes for electrically stimulating different frequency ranges, and a reference electrode part including at least one external electrode being grounded and implantable outside of the cochlea of the user, wherein the plurality of operation electrodes are driven by the processing portion on the basis of the electric acoustic signal, wherein the method comprises
determining an electrode state setting pattern for selecting, according to the operation mode of the cochlear implant system, one of a plurality of electrode state setting patterns, wherein each of the electrode state setting patterns is adapted to enable a stimulation by a stimulation electrode of the plurality of operation electrodes being in a stimulating state and at least one of the plurality of operation electrodes being in a grounded state or in a high impedance state, and
setting, according to the selected electrode state setting pattern, the plurality of operation electrodes into a specified electrode state of a high impedance state, a grounded state and a stimulating state in which a signal based on the electric acoustic signal is supplied to a stimulation electrode of the plurality of operation electrodes,
wherein the stimulating state is defined as a state in which an operation electrode is configured to stimulate with a current,
wherein the grounded state is defined as a state in which an operation electrode is connected to a ground and used as a path for the current to flow from the stimulation electrode.

12. The control method for a hearing device according to claim 11, further comprising
determining an operation mode in which the cochlear implant system currently is or estimating in which operation mode the cochlear implant system is going to be in a predetermined time period, wherein a processing for the determination of the operation mode considers at least one parameter of
- a property of an input electrical acoustic signal,
- an implantation state of the plurality of operation electrodes,
- a functional state of each of the plurality of operation electrodes,
- an instruction input into a configuration setting, and
- an entering into a low power operation mode.

13. The control method for a hearing device according to claim 11, further comprising
selecting as an electrode state setting pattern at least one of:
- in case the operation mode of the cochlear implant system is a safety mode, an electrode state setting pattern causing to set at least one of the plurality of operation electrodes into the stimulated state according to the electrical acoustic signal, and to set all electrodes of the plurality of operation electrodes being located outside the cochlea into the high impedance state,
- in case the operation mode of the cochlear implant system is a focused mode, an electrode state setting pattern causing to set at least one of the plurality of operation electrodes into the stimulated state according to the electrical acoustic signal, to symmetrically set at least two of the plurality of operation electrodes being adjacent to the stimulated electrode into the grounded state, and to set the remaining electrodes of the plurality of operation electrodes into the high impedance state,
- in case the operation mode of the cochlear implant system is a steering mode, an electrode state setting pattern causing to set at least one of the plurality of operation electrodes into the stimulated state according to the electrical acoustic signal, to asymmetrically set at least two of the plurality of operation electrodes being located on one side of the stimulated electrode into the grounded state, and to set the remaining electrodes of the plurality of operation electrodes into the high impedance state,
- in case the operation mode of the cochlear implant system is a virtual electrode mode, an electrode state setting pattern causing to set at least one of the plurality of operation electrodes into the stimulated state according to the electrical acoustic signal, to set each electrode of the plurality of operation electrodes being located on one side of the stimulated electrode towards the distal end of the implant portion into the grounded state, and to set the electrodes of the plurality of operation electrodes being located on the other side of the stimulated electrode into the high impedance state,
- in case the operation mode of the cochlear implant system is a passive full-monopolar mode, an electrode state setting pattern causing to set at least one of the plurality of operation electrodes into the stimulated state according to the electrical acoustic signal, and to set the remaining electrodes of the plurality of operation electrodes into the high impedance state.

14. The control method for a hearing device according to claim 11, further comprising
setting the plurality of operation electrodes into
- the grounded state by causing connecting the respective operation electrode to a common ground of the hearing device,
- into the stimulating state by connecting the respective operation electrode to an electrical signal line supplying a signal generated in accordance with the electrical acoustic signal, and
- into the high impedance state by disconnecting the respective operation electrode from both the common ground and the electrical signal line by driving a plurality of switching elements connected to the plurality of operation electrodes.

15. The control method for a hearing device according to claim 11, further comprising conducting the active grounding procedure for each stimulus being received by the input portion in real time.

16. A computer program product for a computer, including software code portions for performing the steps of claim 11 when said product is run on the computer.

17. The computer program product according to claim 16, wherein
- the computer program product includes a computer-readable medium on which said software code portions are stored, and/or
- the computer program product is directly loadable into the internal memory of the computer and/or transmittable via a network by means of at least one of upload, download and push procedures.

* * * * *